United States Patent [19]
Levy et al.

[11] 4,340,044
[45] Jul. 20, 1982

[54] VOLUME VENTILATOR

[75] Inventors: Donald Levy, River Vale, N.J.; Tibor Rusz, Pittsfield, Mass.

[73] Assignee: Berkshire Research Partners, New York, N.Y.

[21] Appl. No.: 131,920

[22] Filed: Mar. 20, 1980

[51] Int. Cl.³ .............................................. A61M 16/00
[52] U.S. Cl. .......................... 128/204.21; 128/205.15; 128/205.11; 128/205.25
[58] Field of Search ...................... 128/204.21, 204.22, 128/204.23, 205.14, 205.15, 205.16, 203.28, 205.11, 204.24, 205.24, 205.13, 204.19, 204.25

[56] References Cited

U.S. PATENT DOCUMENTS

| | | | |
|---|---|---|---|
| 3,515,134 | 6/1970 | Taylor | 128/205.15 X |
| 3,754,550 | 8/1973 | Kipling | 128/205.16 |
| 3,789,837 | 2/1974 | Philips et al. | 128/205.15 X |
| 3,905,363 | 9/1975 | Dudley | 128/204.24 |
| 3,916,888 | 11/1975 | Buck et al. | 128/204.21 |
| 4,001,700 | 1/1977 | Cook et al. | 128/204.21 |
| 4,096,858 | 6/1978 | Eyrick et al. | 128/204.21 |
| 4,176,663 | 12/1979 | Hewlett | 128/205.16 |

FOREIGN PATENT DOCUMENTS 2745528  4/1978  Fed. Rep. of Germany ........................ 128/204.21

*Primary Examiner*—Henry J. Recla
*Attorney, Agent, or Firm*—Frederick W. Padden

[57] ABSTRACT

A medical ventilator is disclosed for switching and mixing oxygen with air in a driving and oxygen mixing means (2) and delivering the mixture to a gas flow control apparatus (3) for application directly to a patient breathing apparatus (5) or to storage in a bellows reservoir (81) of a continuous positive airway pressure facility (4). The ventilator is equipped with a control module (1) having directly set control adjustments (6–9, 105–112) for determining respiratory rate, inspiration-to-expiration ratio, oxygen concentration and the prescribed minute volume of the oxygen mixture to be delivered to a patient. The adjustment control circuitry which performs the calculations, logic and drive operations for switching and mixing oxygen in plural chambers (14, 18, 29, 30) of module (2), the switching of the mixture through module (3), and sensing fill and refill needs of reservoir (81). Module (4) includes apparatus (83, 84) for exerting a positive pressure on the oxygen in reservoir (81).

30 Claims, 10 Drawing Figures

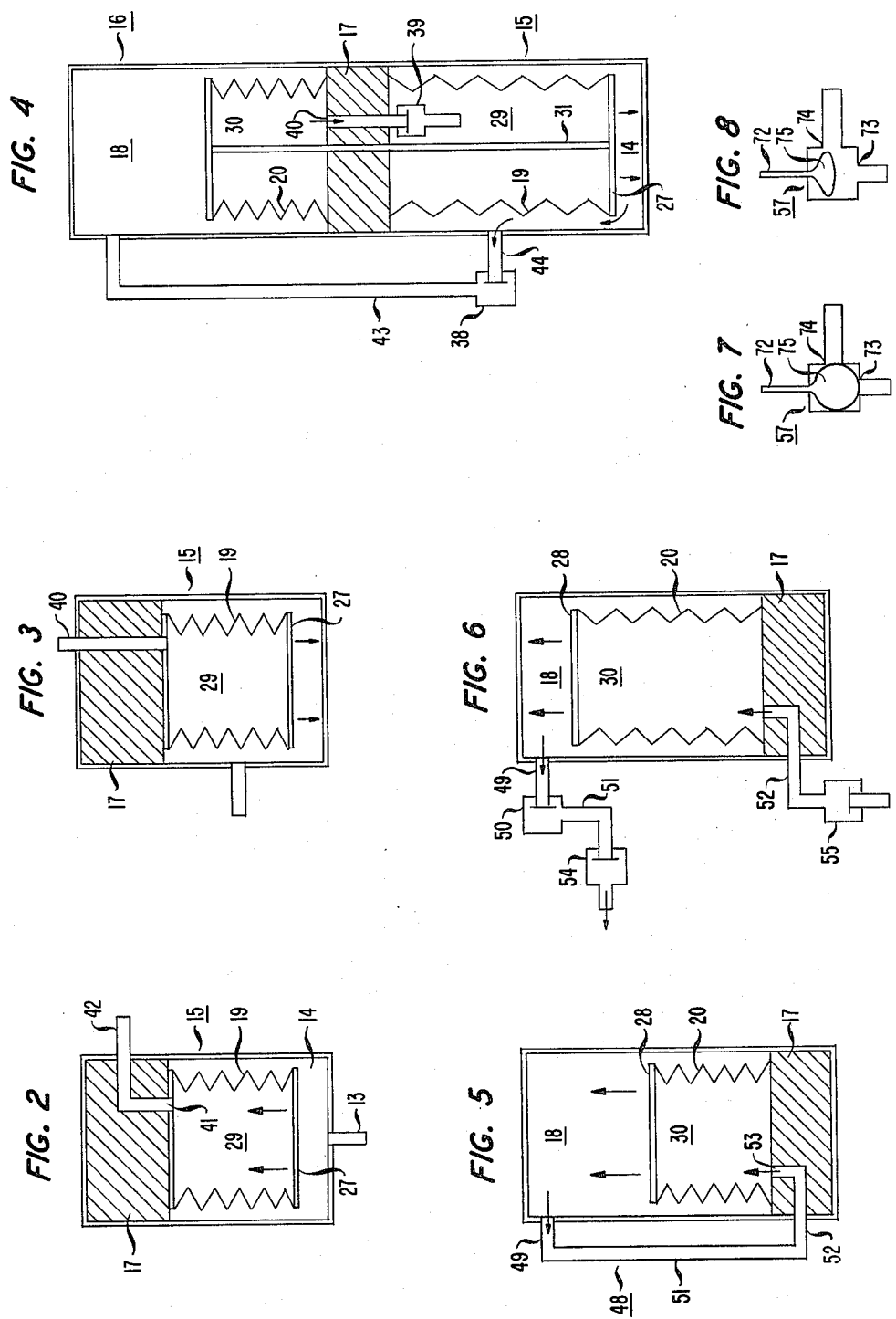

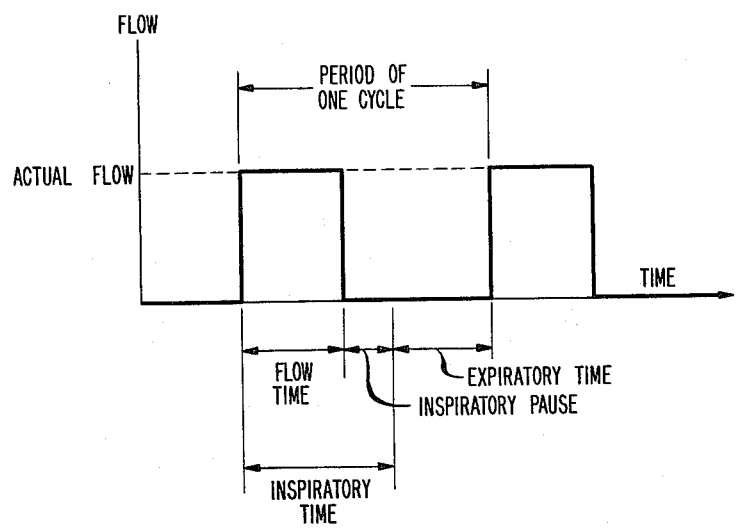

VOLUME VENTILATOR

TECHNICAL FIELD

This invention relates to ventilator equipment for use by patients requiring mechanical ventilatory assistance in intensive care, respiratory care, cardiac care units, and postoperative recovery rooms.

BACKGROUND OF THE INVENTION

A medical ventilator is an apparatus to give artificial respiration. A volume ventilator delivers a given volume regardless of the pressure in the breathing system in which a patient is connected.

Present day mechanical ventilators are typically used in one of five manually selected modes. A first is a control mode in which the patient is totally inactive and patient inhalation is controlled solely by the ventilator. Under such circumstances, exhalation is always passive with no participation by the ventilator except to open a conventional expiratory valve. A second mode is an assist-control technique in which an inspiratory cycle is triggered either by the patient's inspiratory effort, or by the machine, whichever occurs first. Once triggered, the ventilator delivers a selected tidal volume. In a purely assist mode, the inspiratory cycle is triggered only by the patient's inspiratory effort. The machine does not initiate the inspiration automatically. Once the inspiratory cycle is started, the ventilator delivers the full tidal volume. A fourth mode is known as spontaneous in which the ventilator supplies only the breathing gas, and the patient breathes on his or her own without any assistance. A fifth mode is referred to as IMV (Intermittent Mandatory Ventilation). For this mode, the ventilator is set to a very low rate, such as one or two breaths per minute. The ventilator usually delivers as in the assist mode. The reason for the IMV is to assure at least the set amount of ventilation if the patient should decrease breathing spontaneously or should stop breathing altogether.

In present day clinical practice and physiology, ventilation is thought of in terms of minute volume ventilation as a basic parameter. A derivation of minute volume requires a calculation of, for example, tidal volume and respiratory rate.

The presently available and commercially used ventilators are all mechanical devices which are incapable of performing such calculations and are not equipped for the adjustment of the mechanical functions according to the calculated results. As a consequence, prior art ventilators require manual settings of the mechanical functions such as flow, expiration time, inspiration time and the like, rather than the familiar physiological parameters, such as minute volume ventilation. Resultingly, the prior art ventilators have proven very confusing and cumbersome for the average nurse and physician.

DISCLOSURE OF THE INVENTION

Deficiencies of the prior art are ameliorated by the provision of an exemplary embodiment of the invention comprising a volume ventilator having a control module, a pneumatic drive and oxygen mixing module, gas flow control apparatus, an automatic mode control and continuous positive airway pressure facility, and patient breathing apparatus. The exemplary ventilator is equipped for three modes of operation, namely a standby mode, a control mode and an automatic mode. In the standby mode, the ventilator functions to monitor a patient inhalation and exhalation, breathing rate and other parameters. For the standby mode, no gas/oxygen is delivered by the ventilator to the patient. In the control mode, the ventilator automatically delivers to a patient a prescribed minute volume of an air/oxygen mixture at a preset respiration rate and inspiration-to-expiration ratio. The automatic mode is a new modality in which a mandatory minute volume, or MMV, is delivered to a patient for breathing. As the name implies, the MMV mode assures that the patient has adequate ventilation at all times even if his or her own respiratory drive ceases completely.

The control module provides for dial adjustments in physiological terms of minute volume, respiration rate, inspiration-to-expiration ratio, inspiratory plateau, and oxygen concentration. Logic circuitry in the module performs all of the calculations needed for determining the minute volume. The logic circuitry advantageously controls the oxygen mixing and driving module as well as the gas flow control apparatus for determining the duration of inspiration and expiration cycles, the air-/oxygen concentration in the system, and the automatic mode switching operations from spontaneous patient breathing to assisted and/or control mode breathing. The control module receives oxygen from a source and supplies it to the driving and oxygen mixing module in accordance with the set physiological adjustments.

The driving and air oxygen mixing module comprises two cylinders, one for mixing air with the received oxygen and a second for driving the mixture through the gas flow control apparatus to either the automatic mode control and CPAP facility or the patient breathing apparatus. The two cylinders are mounted vertically in opposing directions and are divided from one another by a spacing and channeling block. Each of the cylinders has an interior chamber, each of which houses a flexible bellows. A connecting rod extends through the channeling block and is secured at each of its ends to weighted plates secured to the bellows. This arrangement provides for the compression and expansion of the two bellows in unison, but in opposite directions, and fixes the interior volume of the two bellows. Resultingly, when the interior volume of one bellows is decreasing during a vertical movement, the volume in the other bellows is increasing by the same amount.

The driving cylinder receives oxygen from the control module during an inspiration cycle and utilizes it to move upwardly the driving bellows for forcing an air-/oxygen mixture therein to the gas flow control apparatus. The air/oxygen mixture is placed in the driving bellows during an expiration cycle and from the mixing bellows via a duct in the channeling block and a pressure check valve. The oxygen in the driving cylinder in conveyed to the mixing cylinder via electromagnetic exhaust valve actuated by the control module during the expiration cycle and under the influence of the mixing bellows moving downward under the weight of its plate member and thereby moving the driving bellows within the driving cylinder.

During the succeeding inspiration cycle, the oxygen in the mixing cylinder is transferred to the mixing bellows via an electromagnetic mixing valve actuated under control of the control module. The duration of the valve actuation determines the oxygen mixture with air concentration during the inspiration cycle. When the valve is deactuated and closed, the remainder of the oxygen in the mixing cylinder, if any, is expelled to the atmosphere external to the ventilator and air is drawn into the mixing bellows via a pressure check valve for the remaining duration of the inspiration cycle. At the start of the next succeeding expiration cycle, the air-/oxygen mixture is transferred from the mixing bellows to the driving bellows via a conduit in the channeling block and a check valve for delivery to the gas flow control apparatus during the following inspiration cycle.

The gas flow control apparatus switchably conveys a received gas mixture to either the patient breathing apparatus or the automatic mode control and CPAP facilities. The switching is accomplished by means of an electromechanical valve controllably actuated by the control module. Another electromechanical valve actuatable by the control module switchably drives a patient expiratory valve in the patient breathing apparatus.

The automatic mode control and CPAP facilities provide a flexible bellows assembly for receiving and storing a gas mixture and for supplying that mixture under a constant positive airway pressure to the patient breathing passageway via the gas flow control apparatus. The constant pressure illustratively is developed on the stored gas mixture by a variable pressure source exerting a force on a bellows plate secured to an upper portion of the bellows.

In another embodiment, the bellows is located within a cylinder and the pressure within that cylinder is kept at a prescribed level. That level illustratively is supplied by a blower with a Tee and butterfly valve which restricts the flow and creates the air pressure. Resultingly, the bellows plate moves vertically upward and downward in response to the stored gas mixture and in synchronism with patient breathing.

During patient exhalation in both the control mode and the automatic mode, the diaphragm of the patient expiratory valve is connected to the constant positive airway pressure in the CPAP bellows via the multiport valve of the gas flow control apparatus. As a result, patient exhalation is regulated to exceed only the CPAP magnitude.

For the automatic mode of operation, the patient is enabled to breathe spontaneously from the gas mixture stored in the CPAP bellows and the automatic mode control facilities automatically inform the control module whether such patient breathing is within or without a desired range. To do so, the automatic mode control facilities are illustratively furnished with four individual conductors on a vertical slide bar arrangement and with a wiper arm which is attached to the CPAP bellows plate and which moves vertically over the bar conductors in response to the elevation of the CPAP bellows. A photocell and light source arrangement is advantageously used instead of the bellows slide bar conductors such that the bellows interrupts the light supplied by the source thereby indicating the elevated bellows position. Such an arrangement suitably utilizes three light sources and photocell pickups located at opposite sides of the bellows to detect the bellows interrupting the light paths.

The bellows elevation is indicative of the gas mixture stored therein and of the magnitude of patient breathing in the automatic mode. An electrical signal is applied to the wiper and is conveyed to one of the four bar conductors for alerting the control module of the gas mixture in the CPAP bellows. One of the conductors identifies a low bellows fill due, for example, to heavy patient breathing. When the electrical signal is applied through the wiper to that conductor, the control module is effective to operate the driving and oxygen mixing module for supplying to the CPAP bellows via the gas flow control apparatus a preprogrammed large amount of gas mixture to aid the spontaneous patient breathing.

A second one of the bar conductors identifies that a patient is spontaneously breathing in the desired range. Accordingly, when the wiper couples the electrical signal to that conductor, the control module functions to maintain the preset parameters of the gas mixture minute volume.

A third one of the bar conductors identifies the CPAP bellows is filled due to a patient breathing less than the desired volume during the automatic mode of operation. It significantly indicates a need for assisted breathing and causes the ventilator automatically to reconfigure itself to supply the mandatory minute volume of the gas mixture in synchronism with the patient breathing. The reconfiguration is accomplished when the electrical signal is coupled through the bellows wiper to that third bar conductor for activating the control module for automatically switching the ventilator into an operation such that the inhalation of a patient which is initiated by the patient is equal to the tidal volume corresponding to the dial settings so that a prescribed mandatory minute volume of gas mixture is inhaled by the patient. When the CPAP bellows is in the elevation where the wiper contacts the third conductor bar, each breath is triggered by sensing the patient's spontaneous start of a breath. The ventilator continues to perform this operation as long as the patient breathing requires the mandatory minute volume of assisted breathing. When the breathing returns to the spontaneous range and the CPAP bellows wiper rests on the second bar conductor, the control module is activated for reswitching the ventilator from the triggered operation to the spontaneous patient breathing.

The fourth one of the bar conductors identifies when the CPAP bellows is excessively filled due to a patient breathing much less than the desired spontaneous range. When the electrical signal is connected through the bellows wiper to the fourth conductor, the control module is automatically switched from the automatic to the control mode to supply the mandatory minute volume for patient breathing. The ventilator thereafter remains in the control mode until the patient respiration spontaneously increases to at least the level corresponding to the dial settings.

The gas flow control apparatus is strategically equipped with safety check valves which enable the patient to breathe freely from the atmosphere when a pressure decrease occurs in the patient breathing passageway through the gas flow control apparatus. These valves perform these functions in all modes of ventilator operations.

Flow and pressure signal transducers are located at strategic passageways in the gas flow control apparatus for furnishing electrical signals to the control module. The signals are monitored by the control module and enable it to perform the logic operations needed for ventilator functions including the aforementioned control and automatic mode switching and gas volume control actions. One such flow transducer is located in the inlet passageway between the gas mixture driving bellows and the gas flow control apparatus. A second transducer is located in the inlet passageway to the patient breathing apparatus. A third transducer is located in the expiratory passageway between the patient expiratory valve and the atmosphere external to the ventilator.

A pressure gauge is provided in the gas flow control apparatus for visually displaying the pressure in the inlet passageway to the patient breathing apparatus. In the same passageway, a transducer continuously monitors the airway pressure for providing electrical signal information to the control module for effecting a patient pressure limit not to exceed a desired set limit. Another pressure transducer monitors the CPAP pressure providing electrical signal information to the control module for enabling it to regulate the CPAP pressure in the CPAP facilities. The pressure transducer advantageously is utilizable for regulating the CPAP pressure and the set maximum airway pressure or pressure limit by controlling the opening valve pressure An applique to the ventilator is a nebulizer for utilizing a gas flow for producing an aerosol effect in administering medication. The nebulizer is equipped with automatic timing facilities which are activated by a control device on the ventilator for activating the nebulizer for a fixed time during which the desired flow is supplied to the patient. The control module of the ventilator is advantageously equipped with flow logic which controls the valve driver for reducingly adjusting the total flow supplied to the driving and oxygen mixing module to compensate for the flow introduced by the nebulizer and to insure that the desired flow is supplied to the patient in accordance with the control dial settings. Thus, the minute volume supplied to the patient is the same whether the nebulizer is on or off.

The control module illustratively is equipped with a scaler and calculations circuit which cooperates with the front face controls for minute volume, respiratory plateau, nebulizer, sigh frequency, manual cycle, and manual sigh for producing output electrical signals for calculated tidal volume, rate timing, binary flow, manual breaths and inspiration gating. The scaler and calculations circuit is disabled during the ventilator standby mode of operation and is operative during ventilator control and automatic operating modes. Sigh scaling and calculation functions are enabled during the ventilator control operating mode.

The binary flow signals control valve enable logic in the control module for activating valve drivers circuitry illustratively to, in turn, actuate six valves combinationally for supplying binary weighted valves of flow to the driving and oxygen mixing module. The valve enable logic is enabled by a tidal volume comparator which supplies a flow gate enable signal during the period of actual flow.

The tidal volume comparator compares the calculated tidal volume signal from the scaler and calculations circuitry with an instantaneous tidal volume signal generated by an actual flow integrator. The tidal volume comparator supplies the flow gate enable signal as long as the calculated tidal volume signal is greater than the instantaneous tidal volume signal. During this period, the flow gate enable signal actuates and maintains actuated the exhaust valve in the driving and oxygen mixing module.

The actual flow integrator is initially reset in response to a rate timing pulse from the scaler and calculations circuit to initiate a breathing cycle. It then integrates an actual flow signal received from a summer circuit. The latter combines the binary output flow signals from the valve enable logic with a nebulizer "ON" signal to produce a resultant actual flow signal.

Another tidal volume comparator in the control module compares the instantaneous tidal volume signal from the actual flow integrator with a compensated calculated tidal volume signal from the scaler and calculations circuitry. The compensation is effected by a front face control dial adjustment for oxygen concentration in the range from approximately 21 to 100% oxygen concentration. The desired concentration is achieved by having the comparator actuate an oxygen mixing valve in the driving and oxygen mixing module for combining desired oxygen with air for desired time periods.

The control module is further equipped with nebulizer flow logic which is controlled by a nebulizer switch and an inspiratory flow sensor in the gas flow control apparatus for operating the flow valve driver to reduce the binary weighted flow delivered to the driving and oxygen mixing module by a magnitude equal to that supplied to the patient inhalation by the nebulizer.

A fill monitor circuit is furnished in the control module for cooperating with the automatic mode control and CPAP module for controlling the valve enable logic illustratively to deliver 100 liters per minute flow to the driving and oxygen mixing module whenever the patient breathes more than the magnitude set by the control module dials. The delivered flow reestablishes desired fill in the automatic mode control and CPAP module with the control module actuation of control and expiratory valves in the gas flow control apparatus. The valve actuation is effected by inverter and gate logic under control of the fill monitor. The latter is operated by a fill sensor in the automatic mode control and CPAP module when the patient breaths more than has been set.

The gate logic comprises AND and OR gates for advantageously controlling the expiratory and control valves in the flow control apparatus for assist and control levels of patient breathing. A necessity of operating at the latter levels is sensed by the assist and control level sensors in the automatic mode control and CPAP module. The gates are also enabled by inspiratory logic and comparator circuitry in the control module which are driven by the patient inspiratory flow sensor in the gas flow control apparatus and a sensitivity control dial of the control module.

The control module is further equipped with pressure comparator circuitry for comparing patient inhalation pressure with a prescribed pressure limit and for activating a pressure relief valve when that limit is exceeded.

A servo control arrangement in the control module analyzes pressure in the CPAP module with a CPAP control dial setting for controlling patient CPAP pressure.

DRAWING DESCRIPTION

FIGS. 2 through 8 are functional schematic diagrams depicting operational modes of the structure in FIG. 1;

FIG. 10 depicts waveforms for a cycle of breathing and illustrates the inspiratory period including a flow time with an inspiratory pause and the subsequent expiratory period.

Reference is made to our copending United States Patent Application Ser. No. 11,636 filed Feb. 12, 1979, entitled "Flow Control Equipment," which discloses circuit configurations suitable for use in various circuit components of this application. The disclosure of that application is incorporated herein by reference as though fully disclosed.

DETAILED DESCRIPTION

Figure 1:
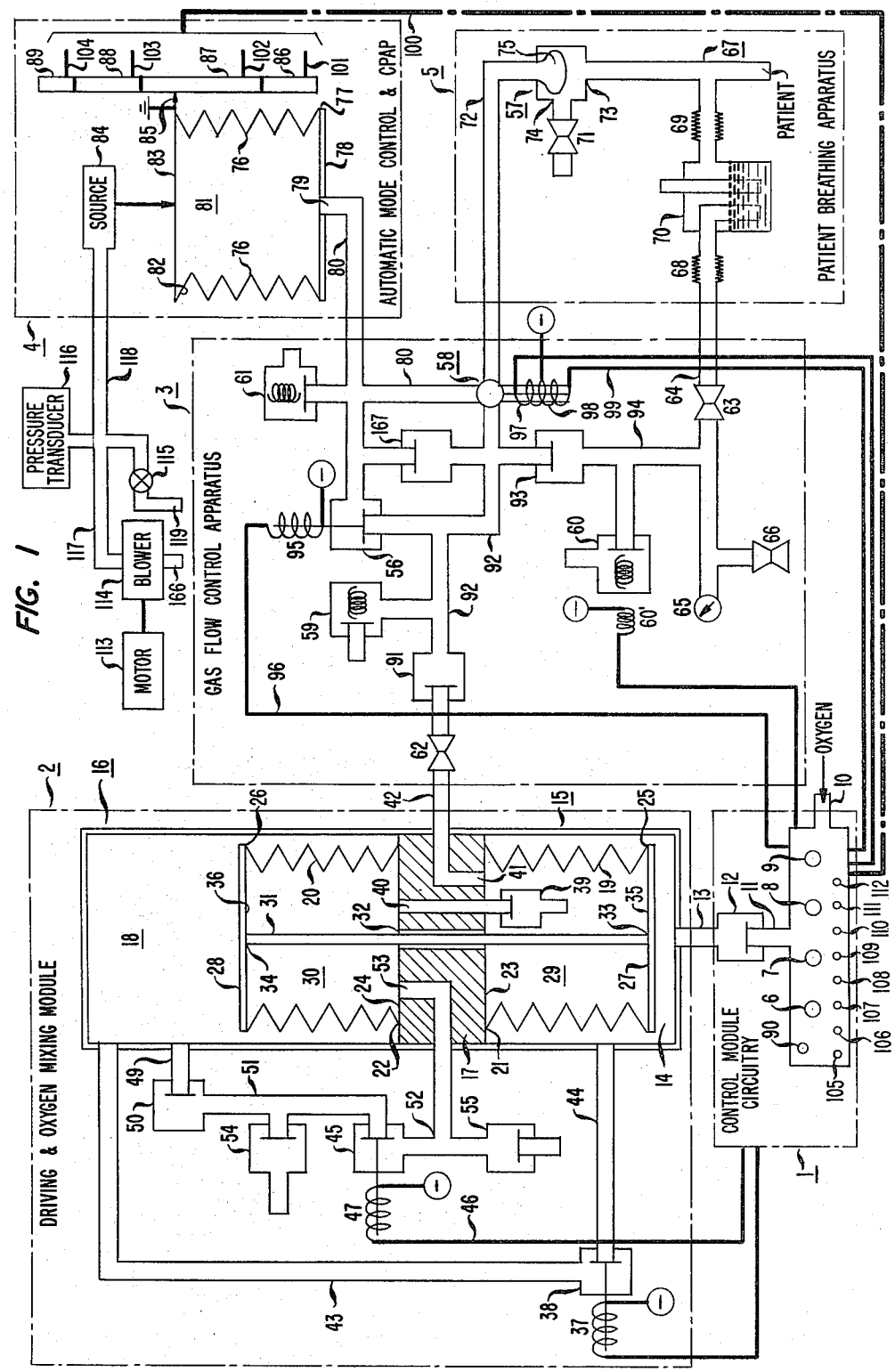
FIG. 1 is a block and schematic diagram of the illustrative volume ventilator.

As shown in FIG. 1, the volume ventilator comprises five basic building blocks including a control module 1, a driving and air/oxygen mixing module 2, a gas flow control apparatus 3, an automatic mode control and CPAP (Continuous Positive Airway Pressure) structure 4, and a patient breathing apparatus 5. Control module 1 is equipped with a plurality of controls 6 through 9 for respectively adjusting minute volume, respiratory rate, inspiration-to-expiration ratio, and the oxygen concentration for the system. Module 1 is furnished with additional control dials and buttons, namely; 105 for sensitivity control in assisted breathing, 106 for patient pressure control, 107 for inspiratory plateau percentage control, switch 108 for timed nebulizer operation, 109 for sigh frequency control, button 110 for manual sigh control, 111 button for manual cycling, 112 for CPAP dial control, and switch 90 for mode selection.

Briefly, module 1 performs several principal functions. A primary function is to deliver an appropriate flow of the driving gas, oxygen, from a source (not shown) via tubes 10 and 11, a check valve 12 and a tube 13 into an interior chamber 14 of a drive cylinder 15. Another function of module 1 is that is furnishes the logic and timed electrical signals for strategically operating the various electromechanical valves utilized in the volume ventilator system.

The mixing module 2 comprises two cylinders 15 and 16 having a respective interior chamber 14 and 18, each of which houses a respective flexible bellows 19, 20. Ends 21, 22 of each such bellows are affixed to a surface 23, 24 of block 17. Free, or movable, ends 25, 26 of each of the bellows 19 and 20 are secured to respective plate members 27 and 28, thus to provide respective inner chambers 29, 30. To fix the interior volume of the two bellows chambers 29, 30, a rigid rod 31 extends through a bore 32 in block 17 and is secured at its ends 33, 34 to facing surfaces 35 and 36 of plate members 27 and 28. The bore 32 has a slightly larger diameter than that of rod 31 so that chambers 29 and 30 are effectively sealed off from one another and so that the bellows 19 and 20 are free to move up and down within the cylinders 15 and 16. Thus, the interior volume of each of the cylinders 15 and 16 is the same. Significantly, the inner volume of the two bellows 19 and 20 is fixed and, because of the interconnecting rod 31, they must move in unison, but in opposite directions. As a consequence, when the volume of bellows 19 is decreasing during an upward travel, the volume within bellows 20 is increasing by the same amount. During a downward travel of bellows 19, its volume increases while that of bellows 20 decreases during its concurrently downward travel.

The operations of module 2 are subdivided into a driving function for both the patient breathing apparatus 5 and the automatic mode control and CPAP structure 4 and an air/oxygen mixing function. The driving function involves inspiration and expiration cycles controllable by the control module 1. The mixing function is effected during the inspiration cycle and is performed in the mixing cylinder 16. During this time the inner chamber 29 of bellows 19 is filled, as explained later, with a prescribed mixture of air and oxygen preparatory to an inspiration cycle.

Referring to FIGS. 1 and 2, an inspiration cycle is now described. Proximate to the start of such a cycle, the control module 1 supplies an electrical signal to complete a circuit path through a winding 37 of an exhaust electromagnetic valve 38 to a negative battery potential for actuating and closing that valve and thereby precluding an exhaustion of oxygen from the interior chamber 14 of cylinder 15. At about the same time, oxygen is applied via the control module 1 and tube 13 into chamber 14 so that the pressure in that chamber and on plate member 27 increases for causing a compression of bellows 19. As soon as the pressure in bellows 19 becomes higher than the opening pressure of a check valve 39 therein, that valve moves upward for closing a communicating bore 40 extending between the inner chamber 30 and chamber 29 via valve 39. The contents of bellows 19 are concurrently extended through a channel 41 in block 17 and a tube 42 to the gas flow control apparatus 3 for delivery to either the CPAP bellows structure 4 or the patient breathing apparatus 5 as explained later. The inspiratory cycle consists of a flow portion as explained above which may be followed by a shorter period, also part of the inspiratory cycle, during which there is no flow. This no-flow period is referred to as inspiratory plateau. At the termination of the flow portion of the inspiration cycle, the check valve 12 closes to seal the interior chamber 14 of cylinder 15. Concurrently, the control module 1 causes the deactuation of the exhaust valve 38 by withdrawing the aforementioned actuating signal. Resultingly, as depicted in FIGS. 1 and 3, the weights of plate members 27 and 29 urge the bellows 19 and 20 downward for effecting an opening of check valve 39 and, in turn, allowing an air/oxygen mixture in chamber 30 to be communicated through bore 40 for filling chamber 29. As the bellows 19 descends, it displaces the previously delivered oxygen from chamber 14 through the exhaust tube 44, valve 38 and tube 43 into chamber 18 of cylinder 16 and until the bellows reach their lower excursion limit and as illustrated in FIG. 4. The delivered oxygen remains in chamber 18 for the duration of the inspiratory plateau period and the expiration cycle preparatory to a mixing-with-air operation which occurs on the next inspiration cycle. The expiration cycle is defined as the period from the end of inspiratory plateau to the start of inspiratory flow.

Module 2 is equipped with facilities for selectively transferring some or all of the oxygen stored in chamber 18 to either the interior chamber 30 of bellows 20 or the atmosphere exterior to the equipment. The transfer occurs during the inspiration cycle when both the check valve 39 for bellows 19 and the exhaust valve 38 are closed as priorly explained during the inspiration cycle.

An oxygen transfer from chamber 18 to chamber 30 occurs in response to both an upward movement of bellows 19 and 20 as priorly described and an actuation of valve 45 for a predetermined time period of the inspiration cycle. The valve actuation is effected in response to an electrical signal supplied by module 1 over conductor 46, as hereinafter explained, to complete a path through a winding 47 of valve 45 to negative battery potential. Upon actuation, valve 45 completes a channel 48 (FIG. 5) for communicating the oxygen from chamber 18 through tube 49, opened check valve 50, tubes 51 and 52 and a conduit bore 53 in block 17 into chamber 30 of bellows 20. A simplified schematic illustration of the structure for the oxygen transfer to chamber 30 is depicted in FIG. 5. The check valve 50 opens automatically and remains open as long as a predetermined differential pressure exists between tubes 49 and 51. Upon module 1 withdrawing the electrical actuating signal from conductor 46, valve 45 is deactuated and closes for, in turn, interrupting further transfer of oxygen to the bellows chamber 30.

Oxygen is expelled from chamber 18 to the atmosphere when valve 45 is not actuated during the inspiration cycle. The channel for expelling the oxygen extends from chamber 18 through tube 49, opened check valve 50, tube 51, and a check valve 54 to the atmosphere. Valves 50 and 54 automatically open and remain open as long as a predetermined differential pressure persists between the atmosphere and the expelling channel. During the oxygen expelling to the atmosphere and in response to the expansion of bellows 20 upward during the inspiration cycle while the mixing valve 45 is closed, air is drawn into bellows chamber 30 via the check valve 55 and tube 52 to mix with the oxygen contents therein. Valve 55 automatically opens and remains open as long as a differential pressure persists between the atmosphere and the bellows chamber 30. A simplified diagram illustrating the oxygen expelling and air intake structure is shown in FIG. 6.

Module 1 controls the duration of the inspiration time during which both bellows 19 and 20 move upward. It also controls the desired concentration of oxygen by simply controlling the opening and closing of the mixing valve 45 for prescribed lengths of time during the inspiration cycle. Illustratively, in a case where an inspiration time is two seconds, and the mixing valve 45 is open half the time, or one-second, the gas entering bellows 20 is half oxygen and half air. Resultingly, a mixture is produced in chamber 30 which is approximately sixty percent oxygen concentration (air being twenty-one percent oxygen).

The mixed gas in bellows chamber 30 is transferred during the succeeding expiratory cycle from chamber 30 to chamber 29 via bore 40 and check valve 39 and thereafter to the gas flow control apparatus 3 during the next following inspiration.

Apparatus 3 performs gas flow switching, the patient expiratory valve driving, safety, sensing, and display control functions. The switching function involves conveying a gas mixture from the input tube 42 either to the patient breathing apparatus 5 or to the automatic mode control and CPAP facilities 4. This switching action is effected by operations of an electromechanical valve 56 under control of module 1 as explained hereinafter. Another function is switchably to drive an expiratory valve 57 in the patient breathing apparatus 5 by means of a multiport electromechanical valve 58 actuated under control of module 1 as later described. Apparatus 3 is equipped for safety functions. One safety function is provided by means of a spring loaded safety valve 59 which enables a patient to inhale from the atmosphere in the event of machine failure to deliver prescribed gas mixtures at predetermined pressures in the gas flow conduit. Another safety function is to limit the pressure in the gas flow conduit to the patient breathing apparatus 5 and the automatic mode control and CPAP facilities 4 by means of variable pressure limiting valve devices 60 and 61. Valve 61 opens to vent the gas flow conduit to the atmosphere when the conduit pressure exceeds a predetermined value fixed by its adjustable spring. Valve 60 performs two functions. One is to limit the patient pressure within the patient breathing apparatus 5 to a maximum safety limit. The second function is to control the pressure to a level set by dial 106 of control module 1. Valve 60 is electrically operated via its winding 60'. Apparatus 3 is furnished with transducer sensors 62 and 63 which function to monitor the gas flow through its input tube 42 and through a patient inspiratory tube 64. A pressure gauge 65 is provided in apparatus 3 for visually displaying the pressure in tube 64 to the patient breathing apparatus 5. A pressure transducer 66 is included for continuously monitoring pressure in tube 64 and providing electrical signal information to the control module 1 for enabling it to regulate the maximum patient pressure in accordance with the dial setting 106. A pressure transducer 116 is included for continuously monitoring pressure in tube 118 and providing electrical signal information to the control module 1 for enabling it to regulate CPAP pressure.

Before further describing the operations of the flow control apparatus 3, it is advantageous first to explain the structural configuration of both the patient breathing equipment 5 and of the automatic mode control and CPAP facilities 4. A patient is connectable to a conventional T-piece 67 which is connected to the patient breathing tube 64 of the flow control apparatus 3 via corrugated hoses 68 and 69 and a gas delivery system 70. The latter is suitably a commercially available heated humidifier arrangement. The other end of the T-piece advantageously is connected to a controlled expiratory valve 57 which controls patient expiration to the atmosphere via an expiration transducer 71 in response to flow pressures in the expiration control tube 72.

In FIG. 1 and as functionally depicted in FIGS. 7 and 8, the expiratory valve 57 is constructed with an inlet 73 attached to the T-piece 67, and outlet 74 connected to transducer 71, and advantageously, a flexible inflatable "mushroom" diaphragm 75 inflatably connected to the expiration control tube 72. Functionally, diaphragm 75 is inflated when the pressure in tube 72 is equal to the pressure in the inlet 73. The inflation occurs as hereinafter explained during inspiration and during portions of the expiration time. During inflation, diaphragm 75 occludes the orifice of inlet 73 as shown in FIG. 7. This occurs because the total surface area of diaphragm 75 facing the orifice of inlet 73 is larger than the surface area of the inlet lumen. Resultingly, the inflated diaphragm 75 presses with more force against the orifice of inlet 73 than the opposing force produced by the pressure at inlet 73 through T-piece 67. As a consequence, the opening pressure of the expiratory valve 57 is controlled by the pressure applied from the inside of diaphragm 75. When that pressure is lower than that at inlet 73, diaphragm 75 deflates to open the expiratory passageway from the inlet 73 to the outlet 74 for expelling a patient expiration through transducer 71 to the atmosphere external to the ventilator. Transducer 71 senses the expired gases and provides signals to the control module 1 for determining expiration flow and volume.

The automatic mode control and CPAP facilities 4 comprise a flexible bellows 76 attached at a lower end 77 to a supporting block 78. The latter is constructed with a bore 79 affixed to a tube 80 coupled to a control valve (CPAP fill valve) 56. Bellows 76 receives a gas mixture from bellows 19 upon an opening of valve 56, as explained later, and resultingly moves upward for storing prescribed volumes of the received gas within its internal chamber 81. An upper end 82 of bellows 76 is secured to an enclosing plate 83 against which is applied an adjustable force from a source 84. The latter suitably comprises a constant torque motor, pneumatic cylinder and piston, a simple weight or bellows 76 may be enclosed in a housing. Source 84, under control of motor 113, blower 114 and a servo valve 115 and transducer 116, produces a positive CPAP pressure upon the gas mixture stored within the bellows chamber 81. Motor 113 operates the blower 114 to supply air flow from inlet 166 via conduit 117, servo valve 115, conduit 119 to the atmosphere. Valve 115, under control of module 1, as later explained, closes or opens until the pressure in conduit 118, as sensed by transducer 116 is equal to the setting of dial 112 of module 1. Changes in the setting of dial 112 cause valve 115 to adjust to maintain the CPAP pressure. Any changes of the motor speed, air density, atmospheric attitude and the like, are all accounted for by the servo control to maintain the dialed-in CPAP pressure.

An electrical ground potential is applied to plate 83 for extension to a wiper arm 85 affixed thereto. Wiper 85 is arranged slidably to move across four fixed and independent vertically aligned conductors 86, 87, 88 and 89 in response to the vertical movement of bellows 76. One of the conductors 86–89 receives the ground potential from wiper 85 upon the elevation of bellows 76 and so as to signal the control module 1 of the volume of gas within bellows chamber 81. The ground potential on wiper 85 is extended to conductors 86, 87, 88 and 89, respectively, to specify the following: (1) fill bellows 76 due to patient breathing more than set minute volume, (2) bellows 76 adequately filled for spontaneous patient breathing, (3) bellows 76 filled by greater amount due to patient breathing less than the set minute volume and breathing assistance required by patient, and (4) bellows 76 filled excessively due to very little patient breathing and switching to controlled patient breathing required.

The ventilator of FIG. 1 is designed to operate in three modes; namely, a standby mode, a control mode and an automatic mode. Preparatory to operating in one of these three modes, the controls 6–9 and 107 of module 1 are set to establish the vital parameters of prescribed minute volume (6), respiration rate (7), inspiratory plateau (107), inspiration-to-expiration ratio (8), and oxygen concentration (9). Resultingly, oxygen is delivered through modules 1 and 2 to the inlet tube 42 of the gas flow control apparatus 3 as priorly explained and at the prescribed air/oxygen mixture, minute volume, respiration rate, inspiratory plateau, and inspiration-to-expiration ratio established by the setting of controls 6–9 and 107.

In the standby mode, a selector switch 90 of the control module 1 is moved to its standby position for disabling the control module circuitry from effecting a delivery of any gas to the driving and oxygen module 2 while the patient monitoring operations continue to function as hereinafter described.

For the control mode of the ventilator operation, a selector switch 90 of module 1 is moved to a position which opens the actuating circuit for the magnetic valve 56 and thereby causes its closing. As a result, all of the gas delivered from bellows 19 to tube 42 during the inspiration cycle of the driving module 2, as priorly described, is directed to the patient via a passageway including transducer 62, check valve 91, tube 92, check valve 93, tube 94, transducer 63, tube 64, hose 68, humidifier 70, hose 69 and T-piece 67. Check valves 91 and 93 automatically open when the pressure of the delivered gas mixture exceeds that within the described passageway leading to the patient. At the same time, the control module 1 actuates the magnetic valve 58 via its energizing winding 97 for connecting the expiratory valve 57 via tube 72 to tube 92 of the described passageway to the patient. As a consequence, pressure within the mushroom diaphragm 75 is the same as in the patient passageway and thereby inflates diaphragm 75 for closing the lumen of inlet 73 so that all of the gas supplied by bellows 19 and the described passageway is delivered to the patient.

During the expiratory cycle of the driving module 2 operating, the control module 1 actuates valve 58 via its second energizing winding 98 for switching the expiratory valve diaphragm 75 from tube 92 into connection with the CPAP bellows 76 via tubes 72 and 80. Accordingly, the opening pressure of the expiratory valve 57 decreases to the CPAP pressure maintained in bellows 76. Thus, diaphragm 75 deflates for opening valve 57 and the patient exhales through transducer 71 to the atmosphere until the pressure at inlet 73 becomes proximately equal to the CPAP pressure of bellows 76.

If, during operation in the control mode, the volume of gas in bellows 76 drops sufficiently for any reason, wiper 85 slides onto the bellows fill conductor 86 for signaling the control and driving modules 1 and 2 to actuate and open valve 56 so that a predetermined larger volume of gas is delivered to bellows 76 via tube 80 for maintaining the prescribed CPAP function with wiper 85 on the spontaneous breathing conductor 87.

The automatic mode of the ventilator operation is established by operating the selector switch 90 of control module 1 to a second position for thereby effecting an operation of valves 56 and 58 of FIG. 1. Valve 56 operates over a path extending from negative battery potential through the valve energizing winding 95 and conductor 96 to an electrical signal (not shown) supplied by module 1. Upon operating, valve 56 provides a conduit for extending the prescribed minute volume of gas mixture from the interior chamber 29 of bellows 19 to the interior chamber 81 of bellows 76 via a path from chamber 29 through opening 41, tube 42, transducer 62, check valve 91, tube 92, valve 56, tube 80 and bore 79.

The last-mentioned operation of valve 58 is effected over a path from negative battery potential through a second one of the valve energizing windings 98 and conductor 99 to an electrical signal (not shown) supplied by module 1. In operating, valve 58 is effective to couple the interior chamber 81 of bellows 76 to the inflatable diaphragm 75 of the expiratory valve 57 over a path including tube 72, valve 58, tube 80 and bore 79. Resultingly, diaphragm 75 is inflated due to equal pressures in tube 72 and the inlet 73 of valve 57. Thus, the airway pressure and the opening pressure of the expiratory valve 57 are the same as the pressure in chamber 81 of the CPAP bellows 76.

Thereafter, a patient connected to the T-piece 67 can breathe freely from the CPAP bellows 76 via tube 80, check valves 167 and 93, tube 94, transducer 63, tubes 64 and 68, humidifier 70, tube 69 and T-piece 67, advantageously at any time rather than under control of the control module 1 and driving and mixing apparatus 2. Bellows 76 functions essentially as a reservoir for the gas mixture breathed by the patient. It is replenished in bellows 76 by the driving apparatus 2 continuously delivering the set minute volume of gas mixture at the respiration rate and inspiration-to-expiration ratio set by controls 6-9 of module 1. During patient exhalation, the expiratory valve 57 is opened for enabling the patient to exhale through transducer 71 to the atmosphere. The valve opens as a result of the pressure at its inlet being greater than that in tube 72. The pressure differential across check valve 93 during patient exhalation also causes it to close which insures that all of the exhalation is through exhalation valve 57 and transducer 71 to the atmosphere.

Several conditions may occur during patient breathing. For example, the patient may breathe more or less than the minute volume set by control 6. If the patient breathes more, the level of bellows 76 drops as priorly explained, and wiper 85 extends ground to conductor 86 and over a lead 101 of cable 100 for signaling the control module 1 to supply a preprogram larger volume of gas mixture through apparatus 2 and 3 to bellows 76 so that it operates in the spontaneous breathing range with wiper 85 on conductor 87. When wiper 85 rests on that conductor, ground is supplied over lead 102 of cable 100 for signaling the control module to supply the gas mixture needed for patient breathing.

Automatic breathing assistance is given to the patient when bellows 76 excessively fills and resultingly signals that the patient is breathing less than the prescribed minute volume. When bellows 76 fills to the extent that wiper 85 slides into contact with conductor 88, the control module 1 is signaled over lead 103 of cable 100 to that effect and, if the control module concurrently senses a flow signal through transducer 63, module 1 deactuates and closes valve 56 by withdrawing the energizing signal from the conductor 96. Concurrently, module 1 deenergizes winding 98 and energizes winding 97 of valve 58 as priorly explained for connecting the expiratory valve diaphragm 75 via tube 72 to tube 92. This switchover operation causes the remaining portion of the tidal volume to be delivered from the driving bellows 19 directly to the patient. Consequently, the patient triggered the inspiration by breathing less and the ventilator increases the depth of the breath in synchronism with the patient breathing. Switchback to the automatic mode of the ventilator operation is effected when the bellows fill decreases to the point where wiper 85 rests again on conductor 87 and a ground signal is applied thereover to conductor 102 for causing module 1 to reenergize valves 56 and 58 to again establish the automatic mode of operation, as already explained.

If the patient breathes very little or not at all, bellows 76 fills to a level which causes the ventilator tow switch automatically to its control mode of operation. This action occurs when bellows 76 fills to the point where wiper 85 slides over contact 88 to contact 89. As wiper 85 slides over contact 88, it effects the automatic switchover to assisted breathing, as already described. When wiper 85 slides onto conductor 89, it effects the automatic switchover to control breathing. When wiper 85 slides onto conductor 89, it extends the ground signal over lead 104 of cable 100 to the control module 1 for signaling it to switch the ventilator into its control mode of operation with subsequent patient breathing directly from the driving bellows chamber 29.

Figure 9:
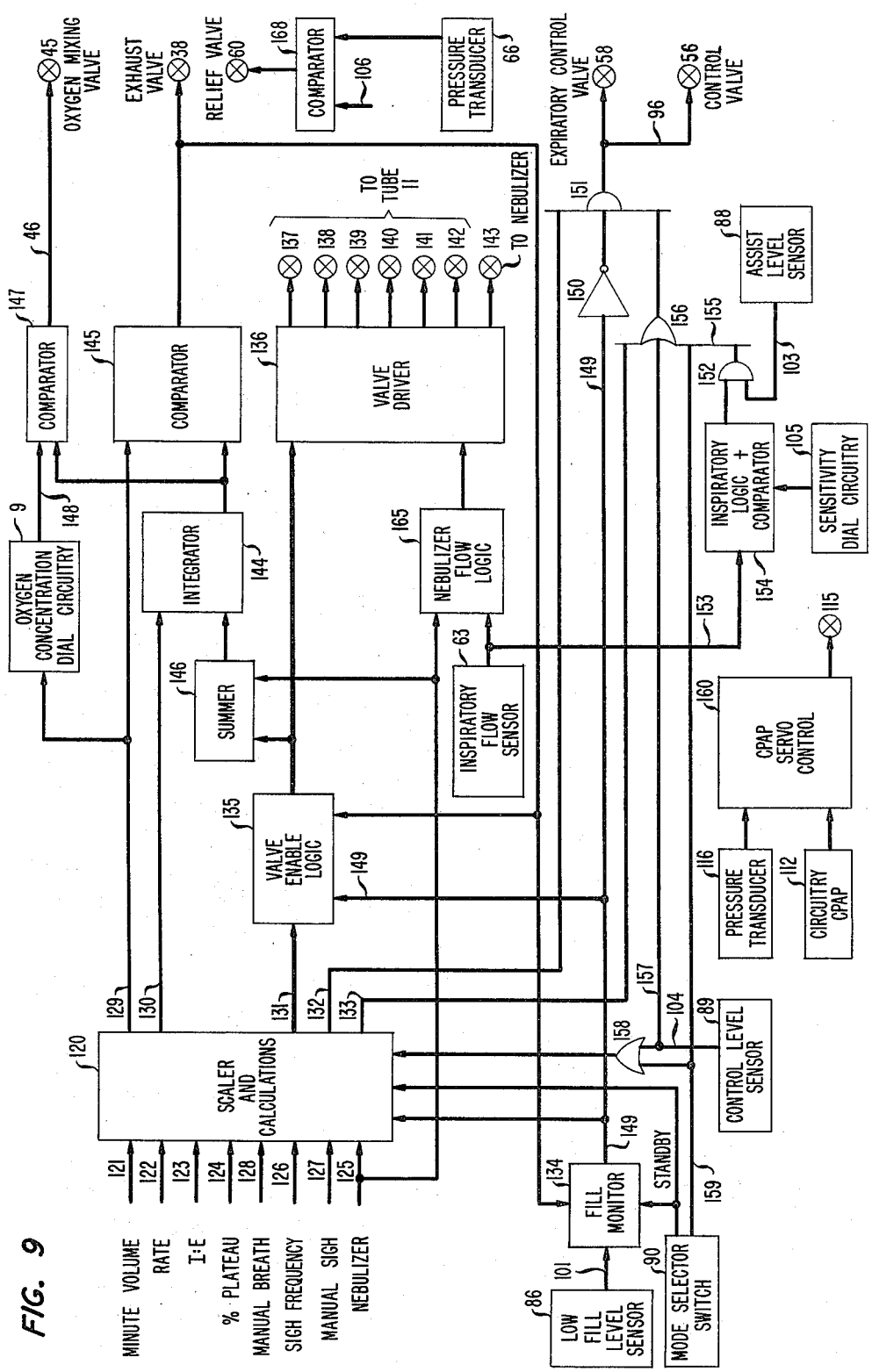
FIG. 9 is a block schematic diagram of the control module of FIG. 1.

Turning now to FIG. 9, the circuitry of control module 1 for controlling its flow control valves as well as the strategic flow valves in the driving and oxygen mixing module 2, gas flow control apparatus 3 and the automatic mode control and CPAP module 4 is now described. Module 1 is equipped with a scaler and calculations circuit 120 which receives dial-in, switch and pushbutton electrical data on input conductors 121 through 128 for scaling and conversion into calculated output voltages and other electrical signals on conductors 129 through 133 for the flow control and timing operations. A tabulation of the dial, switch and pushbutton devices, together with illustrative range or setting information and the conductor on which the functional data is received is as follows:

| DEVICE | RANGE OR FUNCTIONAL SETTING | INPUT CONDUCTOR |
| --- | --- | --- |
| Minute volume dial 6 | 2 to 30 liters/minute | 121 |
| Respiratory rate dial 7 | 6 to 40 breaths/minute | 122 |
| Inspiration-to-expiration dial 8 | 1:1 to 1:4 | 123 |
| Inspiration plateau dial 107 | 0 to 40% of inspiratory time, during which time there is no flow and no patient exhalation. | 124 |
| Nebulizer switch 108 | Controls a connection of a nebulizer to the patient inhalation line for a timed period. | 125 |
| Sigh frequency rotary switch 109 | OFF, 32, 64 and manual positions operatively corresponding to every 32 or 64 breaths automatically or manually under control of pushbutton 110 and conductor 127. Sigh has the effect of increasing the tidal volume of a particular breath by 50% with a maximum 2-liter tidal volume. | 126 |
| Manual cycle pushbutton 111 | Manual initiation of a start of a respiratory cycle. | 128 |

A tabulation of the calculated outputs from circuit 120 together with a brief description of the output signals and the conductors on which they are supplied is as follows:

| CALCULATED OUTPUT | DESCRIPTION | OUTPUT CONDUCTOR |
| --- | --- | --- |
| Tidal volume voltage | A voltage corresponding to the tidal volume and proportional in magnitude to minute volume/rate. Voltage limited to the value corresponding to 2 liters. | 129 |
| Rate timing pulse | A short pulse (approximately 10 milliseconds nominal) which is used to initiate a breathing cycle. The interval between successive pulses is related to the rate dial setting by interval in seconds equal to 60/rate. | 130 |
| Binary flow signal | Multidigit binary number voltages corresponding to the actual flow required during the flow portion of the inspiratory cycle. This flow signal is proportional | 131 |

| CALCULATED OUTPUT | DESCRIPTION | OUTPUT CONDUCTOR |
|---|---|---|
| | to $$\frac{MV\left(1 + \frac{E}{I}\right)}{1 - \% \text{ plateau}}$$ when the nebulizer is "OFF" and proportional to $$\frac{MV\left(1 + \frac{E}{I}\right)}{1 - \% \text{ plateau}} -$$ nebulizer flow when the nebulizer is "ON". Illustratively, the nebulizer flow is approximately 10 liters/minute. The binary number is in 2 liters/minute steps and has a value which is limited to 100 liters/minute. The signal is on 6 lines represented by conductor 131 and corresponds to 2, 4, 8, 16, 32 and 64 liters per minute. | |
| Inspiratory gate signal | A voltage whose duration is equal in seconds to 60/Rate (1 + Expiration/Inspiration) which is the total inspiratory period including any inspiratory plateau. | 132 |

Turning now to FIG. 10, it illustrates a somewhat idealized waveform of a cycle of breathing for illustrating the inspiratory pause portion of the inspiratory time in relation to the actual flow portion of inspiration. Thus, inspiration time is divided into two parts, namely flow time and inspiratory pause. During flow time actual flow takes place and during the pause, there is no flow. During the total inspiratory time, the exhalation valve 57 of FIG. 1 is closed. This action serves to keep the patient's lung expanded for the inspiratory pause.

The inspiratory pause is expressed as a percentage of the total inspiratory time I. Using the parameters F=flow, MV=minute volume, and E=expiratory time and t=inspiratory pause, the following relationship is derived:

$$F = \frac{MV\left(1 + \frac{E}{I}\right)}{\left(1 - \frac{t}{I}\right)}$$

With no inspiratory pause, t=0 and the relationship reduces to $$F = MV(1 + E/I).$$

The range of t/I as utilizable in the ventilator is 0 to 40% and is controlled by the inspiratory plateau dial 107 of FIG. 1. For a given setting of MV and I:E ratio by controls 6 and 8 of FIG. 1, the flow F is increased with the increasing percentage of inspiratory plateau as the actual flow is "ON" for a shorter portion of the inspiratory time. The inspiratory plateau control 107 is illustratively a potentiometer which forms part of a voltage divider (not shown) circuitwise incorporated into the scaler and calculations circuit 120 of FIG. 9.

Utilization of the foregoing in the control module 1 is, by a derivation of two flows, as follows:

$$f_1 = MV\left(1 + \frac{E}{I}\right) \text{ and}$$

$$f_2 = \frac{MV\left(1 + \frac{E}{I}\right)}{\left(1 - \frac{t}{I}\right)}$$

The first flow $f_1$ defines the "I" time by an integration of an electrical value of $f_1$ until the calculated tidal volume TV=MV/Rate is reached. The second flow $f_2$ defines the actual output flow from the valves 12. Flow $f_2$ is greater than $f_1$ causes the tidal volume to be reached before the inspiratory time I and is the actual inspiratory portion of I.

The three different modes of the ventilator operation are selected by the mode selection switch 90 depicted by a block in FIG. 9. In the standby mode, switch 90 supplies a signal for disabling the operation of the scaler and calculations circuit 120 and the fill monitor circuit 134. Resultingly, output 131 of circuit 120 controls the valve logic 135 and valve driver 136 for deactuating the flow valves 137 through 142 and thereby blocking the flow of gas via tube 11, check valve 12 and tube 13 to the driving and oxygen mixing module 2. The remainder of the ventilator operations for patient monitoring such as inhalation, exhalation, breathing rate and the like are functional as hereinafter described for the automatic and control modes of operation.

In the automatic mode and with the CPAP wiper 85 in contact with bar conductor 87 of FIG. 1, the operation is as follows: Starting at the beginning of an inspiration cycle, the scaler and calculations circuit 120 supplies a rate timing pulse over conductor 130 for resetting the actual flow integrator 144 and, in turn, its output to zero. Comparator 145 compares the calculated tidal volume signal received from circuit 120 over conductor 129 with the output of integrator 144. Initially, the integrator output is less than the calculated tidal volume and, resultingly, comparator 145 generates a flow gate voltage at its output for controlling the exhaust valve 38 of module 2, valve enable logic 135, and fill monitor 134 of FIG. 9.

The flow gate voltage actuates and closes the exhaust valve 38 and thereby precludes an exhaustion of oxygen from chamber 14 of module 2, as priorly explained.

Concurrently, the flow gate voltage enables the logic circuitry 135 to pass the binary number signals from circuit 120 to activate the valve driver 136 and, in turn, to actuate prescribed ones of the flow valves 137–142 which supply oxygen to module 2 of FIG. 1 via tube 11, check valve 12 and tube 13.

The digital signals from the logic circuitry 135 are summed with a nebulizer signal from a nebulizer switch 108 in a summing circuit 146. The resultant sum output signal which is proportional to the actual flow is directed to the input of integrator 144. Flow from module 1 to module 2 via tube 11, check valve 12 and tube 13 continues until the output of integrator 144 is equal to the calculated tidal volume, at which time the flow gate signal is withdrawn by comparator 145. As a result, logic circuitry 135 is disabled and, in turn, deactivates the valve driver 136 to close the actuated ones of the valves 137–142. This action represents the end of the flow. At about the same time, valve 38 of FIG. 1 deactuates in response to the removed flow gate signal. No further flow from module 1 to module 2 occurs until after the integrator 144 is reset to zero by the rate timing signal pulse for initiating another cycle.

The aforementioned nebulizer switch 108 is effective to produce a reduced flow signal from scaler and calculations circuit 120 to the valve enable logic 135 and driver 136 whenever the nebulizer is "ON." The magnitude of the reduction is essentially equal to the magnitude of the flow introduced by the nebulizer into the patient inhalation path via the patient breathing apparatus 5 of FIG. 1. Driving gas for the nebulizer is supplied from valve 143 which is controlled by nebulizer flow logic 165. In order for valve 143 to be actuated, two conditions exist: (1) nebulizer control switch must be closed ("ON") and (2) flow must be present at inspiratory flow sensor 63.

At the aforementioned beginning of the inspiration cycle, the control module 1 is effective to actuate the oxygen mixing valve 45 of module 2 (FIGS. 1 and 9) for enabling a transfer of a prescribed concentration of oxygen from chamber 18 to chamber 30, and selectively, from chamber 18 to the atmosphere, as priorly described. In FIG. 9, valve 45 is actuated in response to an output signal from a tidal volume comparator 147, which signal is generated just following the resetting of the flow integrator 144 of FIG. 9 by the rate timing pulse on conductor 130 at the beginning of the inspiration cycle, as already explained. Comparator 147 compares the flow integrated output of integrator 144 with a compensated value of the calculated tidal volume signal on conductor 129. The compensation is effected by the oxygen concentration dial circuitry 9 which suitably comprises a variable voltage divider serially between conductor 129 and one of the compare inputs 148 of comparator 147. The dial 9 is settable between 21 and 100% oxygen as hereinbefore described, which setting actually sets a voltage on input 148 that is a proportion of the calculated tidal volume on conductor 129. If the latter voltage is equal to the tidal volume voltage on conductor 129, dial 9 is set to 100% for 100% oxygen. If voltage on input 148 is equal to zero, dial 9 is set to 21% for air concentration in chamber 30.

As long as the tidal volume voltage output of the flow integrator 144 is less than the voltage on input 148, the output of comparator 147 actuates and maintains actuated the valve 45. At the point where the voltages are equal, the comparator 147 output changes state for effecting a deactuation of valve 45 and causing oxygen from chamber 18 to be expelled to the atmosphere via check valve 50 and 54 of module 2, FIG. 1, as priorly explained. Concurrently, air is drawn into bellows chamber 30 of module 2 via check valve 55 of FIG. 1, as already described, and for the duration of the flow gating signal from the output of comparator 145. The latter signal occurs as priorly described until the prescribed tidal volume has been supplied.

The foregoing describes ventilator operations when the patient is breathing the same amount as the minute volume set by dial control 6 and effectively, the gas in chamber 81 of FIG. 1 is essentially constant, and wiper 85 is in contact with bar conductor 87. The following description explains ventilator operations for situations where the patient breathes more and less than the minute volume set by dial control 6.

When the patient breathes more than the set minute volume, the wiper 85 of FIG. 1 contacts the low fill level sensor conductor 86 as bellows 76 descends due to the emptying of chamber 81, as priorly described. As a consequence, ground potential is applied over conductor 101 for operating the fill monitor circuit 134 of FIG. 9 to produce an output fill signal on conductor 149 immediately upon the removal of the flow gating signal of comparator 145 which theretofor had maintained the fill monitor 134 reset. The fill signal on conductor 149 is effective to:

(1) activate the scaler and calculations circuitry 120 of FIG. 9 for setting the calculated tidal volume signal on conductor 129 to 2 liters and to initiate a new breathing cycle, (2) operate the valve enable logic circuitry 135 of FIG. 9 for producing 100 liter/minute binary signals (64, 32 and 4 liter binary signals) to the valve driver 136, thus to override the binary flow signals supplied by circuitry 120 and to produce a 100 liter per minute flow from module 1 to module 2, and (3) actuates the control valves 56 and 58 of FIG. 9 via inverter 150 and the AND gate 151 so that the flow in FIG. 1 from chamber 29 is only directed to chamber 81, as priorly described. This fill action serves to cause bellows 76 to return rapidly to a filled state. This fill cycle prevents the bellows 76 from becoming empty which, in turn, would cause the patient to receive inhalation via bypass valve 59 of FIG. 1. If the patient breathed through valve 59, the oxygen percentage would be that of air, and any CPAP pressure from source 84 of FIG. 1 would not be available to the patient, and the patient would be inhaling at atmospheric pressure.

When the fill cycle is completed, the wiper 85 of FIG. 1 has moved from bar conductor 86 to 87 and, in turn, controls the fill monitor 135 for withdrawing the fill signal from conductor 149. At the completion of this priorly described fill cycle, the aforementioned operations for patient breathing while wiper 85 rests on bar conductor 87 are resumed.

When a patient breathes less than the minute volume set by dial control 6, patient assist breathing is prescribed, and the ventilator takes such action in response to wiper 85 contacting assist level sensor conductor 88 of FIG. 1 as a result of continuous gas delivery to chamber 81 exceeding the patient inhalation. Essentially, chamber 81 receives more gas than the patient inhales and bellows 76 rises. The signal from sensor 88 is directed to AND gate 152 and when the patient next initiates a breath, this effort is detected by flow sensor 63 of FIGS. 1 and 9. The output of sensor 63 is extended over conductor 153 to the inspiratory logic and comparator 154 which integrates the sensed flow and compares the resulting volume output signal voltage to a preset voltage. (Typically corresponding to 100 to 200 cc. of volume.) When the preset volume is reached and the flow through sensor 63 is greater than a threshold voltage derived from the sensitivity dial 105, the output of comparator 154 in conjunction with the signal from sensor 88 causes output of AND gate 152 to be directed over conductor 155 through OR gate 156 to AND gate 151. The latter gate is fully enabled in response to an inspiratory gate enable signal on conductor 132, the absence of a fill signal on conductor 149, and the aforementioned output of OR gate 156 causing valves 57 and 58 to close during the inspiratory cycle. Closure of valve 56 serves to direct the tidal volume from chamber 29 directly to the patient via tube 42, transducer 62, valve 91, tube 92, check valve 93, sensor 63, tube 64 and the humidifier 70. Closure of valve 58 causes the pressure in mushroom chamber 75 of valve 57 to assume the same pressure existing at inlet 73 of valve 57, causing inlet 73 to be occluded. Resultingly, the aforementioned tidal volume from chamber 29 is delivered directly to the patient.

If the patient does not initiate a breath for the foregoing "assist" breathing, wiper 85 with control level sensor conductor 89 thereby supplies a signal to conductors 104 and 157 for extension through OR gate 156 to AND gate 151. Upon enablement, gate 151 causes valves 56 and 58 to close for directing the flow directly from chamber 29 to the patient as described in the immediately preceding paragraph. The signal on conductor 104 is extended through OR gate 158 for enabling the sigh function (50% increase in tidal volume). This action occurs at the inspiratory period immediately following the wiper 85 contact with conductor 89 independent of the patient's effort to initiate a breath. The action is that of completely controlled ventilation rather than assisted ventilation. If the patient starts to breathe more than the dial settings on module 1, the bellows 76 will fall, and the ventilator operations will return to those previously described.

Turning now to the control mode of the ventilator operation, the selector switch 90 of FIG. 9 is moved to its control position for effecting patient breathing in a controlled manner. The mode selector switch extends a signal over conductor 159 to OR gate 156 for overriding the effects of all the inputs to that gate as previously discussed. In order to maintain CPAP operation, bellows 76 of FIG. 1 must not be empty and the "fill" cycle, as already explained, functions in a manner as previously described. A signal on conductor 159 also is extended via gate 158 to enable the sigh function.

When the ventilator is in the control mode, the sigh function (50% increase in tidal volume) operates in accordance with dial control 109. In the standby, or automatic mode of the ventilator, the sigh function is inoperative because the flow is directed to the CPAP bellows from which the patient is normally initiating breaths. The sigh function is also interlocked with the signal from sensor 89 via OR gate 158 so that if the patient lapses into a controlled breathing as sensed by sensor 89, the sigh is enabled. The manual sigh button 110 initiates a sigh cycle as described whenever the sigh function is enabled and button 110 is actuated.

Anytime the manual cycle button 111 is depressed, a controlled breath is delivered to the patient under control of circuit 120, OR gate 156 and AND gate 151 as well as valves 56 and 58, as previously described.

FIG. 9 shows a CPAP servo control circuit 160 which receives two voltage inputs, the first of which is derived from the pressure transducer 116 of FIG. 1 and the second from the circuitry including the CPAP electrical control dial 112. The latter illustratively is settable in the range from 0 to 20 centimeters $H_2O$. If the CPAP dial 112 voltage is different than the voltage from pressure transducer 116, circuit 160 causes servo valve 115 to alter the restriction of the flow for causing the pressure directed to source 84 to change so that the transducer 116 voltage is equal to the dial 112 setting voltage.

FIG. 9 shows a patient pressure limit control system comprising relief valve 60, comparator 168, pressure limit dial circuit 106 and a patient pressure transducer 66. If the pressure transducer voltage exceeds the voltage corresponding to the setting of dial 106, comparator 168 actuates relief valve 60 which causes a reduction of pressure in tube 94 (FIG. 1) by venting the gas in that tube to the atmosphere.

The design of this ventilator is such that all of the input and output parameters of the scaler and calculations circuit 120 of FIG. 9 are available for compiling a record of the settings and derived parameters by means of a suitable recorder (not shown). The flow sensors 63 and 71 of FIG. 1 are monitorable for determining and recording the flow to and from the patient. These flows are integratable and processed for displaying volumes. A comparison of the volumes to and from the patient allow for a detection of any leak in the patient connection and the actuation of an alarm. A list of the available monitored signals from the ventilator include: set minute volume, set rate, set inspiration-to-expiration ratio, set inspiratory plateau, nebulizer signal on-off, sigh setting; Mode: standby, auto or control, set % oxygen, CPAP setting, calculated tidal volume, calculated flow, actual flow (binary signals) from circuit 120 of FIG. 9, sigh activation, CPAP pressure via transducer 116, patient pressure via transducer 66, actual flow, total inspiratory period, signals to indicate a fill, assist and control cycle.

The front panel of the ventilator is suitably equipped with devices for furnishing visual indications of mode and operation status of the ventilator and for certain alarm functions. These include: standby, assist or control modes of operation, spontaneous breathing, CPAP on-off, airway pressure meter, sigh indicator for when sigh is taking place, oxygen enriched (when oxygen is greater than 21%), nebulizer on, patient breath trigger of ventilator, patient pressure alarm to indicate when patient tried to exceed the setting of dial 106 of FIG. 1 (transducer 66 signal utilizable for comparison with dial 106 setting), dial setting exceeds specifications alarm when settings call for greater than 2 liters per minute, temperature readout of airway to patient, fill empty humidifier, power failure, and ventilator inoperative.

What is claimed is:

1. A volume ventilator for artificial ventilation of a patient during inspiration and expiration cycles of the ventilator comprising patient breathing apparatus, gas flow control apparatus operably connected to said patient breathing apparatus for supplying a delivered air/oxygen gas mixture to said breathing apparatus, a driving and air/oxygen mixing means operably connected to said flow control apparatus and controllable for delivering a prescribed mixture of air/oxygen gas to said flow control apparatus, and control means operably connected to said flow control apparatus and said driving and air/oxygen mixing means including adjustment means cooperating with said flow control apparatus and said driving and air/oxygen mixing means for setting a prescribed minute volume, respiratory rate and inspiration-to-expiration ratio, said control means comprising control circuitry activated by settings of said adjustment means for furnishing control signals corresponding to said prescribed minute volume, respiratory rate and inspiration-to-expiration ratio for controlling the driving and air/oxygen mixing means to mix and deliver said air/oxygen gas mixture to said gas flow control apparatus and for controlling the operation of said gas flow control apparatus for supplying to said patient breathing apparatus said air/oxygen gas mixture at said prescribed minute volume, respiratory rate and inspiration-to-expiration and the air/oxygen concentration of said predetermined volume of air/oxygen gas mixture, said driving and air/oxygen mixing means comprises a driving chamber, said control means comprises a plurality of flow valve means actuable for delivering oxygen gas from a source to said driving chamber, said control circuitry further comprises circuitry responsive to furnished ones of said control signals for actuating predetermined ones of said valve means for delivering said oxygen gas to said driving chamber during an inspiration cycle of said ventilator, and said driving and air/oxygen mixing means further comprises a driving chamber for receiving said oxygen under pressure during an inspiration cycle of the ventilator from said supplying means, a storing chamber for storing the oxygen receivable from said driving chamber, valve means controlled by said control circuitry during an expiration cycle of said ventilator for communicating the oxygen from said driving chamber to said storing chamber, a mixing bellows mounted within said storing chamber and having an interior bellows mixing chamber for storing an air/oxygen mixture, valve means controlled by said control circuitry during an inspiration cycle of said ventilator for communicating some or all of the oxygen from said storing chamber to said bellows mixing chamber, valve means actuatable during an inspiration cycle of said ventilator in response to differential pressures for exhausting oxygen in said storing chamber to the atmosphere and for mixingly admitting air into said bellows mixing chamber, a drive bellows mounted within said driving chamber and having an interior drive bellows chamber for storing an air/oxygen mixture, means operable during an expiration cycle of said ventilator for communicating the air/oxygen mixture from said bellows mixing chamber to said drive bellows chamber, means communicating the air/oxygen mixture in said drive bellows chamber to said gas flow control apparatus;

a spacing member spaced between said driving and storing chambers and having first and second surfaces each of which is affixed to a fixed end of said mixing and driving bellows, plate members each of which is secured to a respective movable end of each respective said bellows for providing respective inner chambers, and a rigid rod extending through a bore in said spacing member and secured at ends of said rod to facing surfaces of said plate members.

2. The volume ventilator of claim 1 further characterized in that said driving and air/oxygen mixing means (2) further comprises an exhaust valve (38) controllable for exhaustingly communicating oxygen gas from said driving chamber (14) to said storing chamber (18), and said control circuitry (1) further comprises exhaust control circuitry (144, 145, 146) responsive to a receipt of control signals from said calculations circuitry (120) and flow control signals from said valve means actuating circuitry (135) for controlling said exhaust valve (38) to effect the communication of said oxygen gas from said driving chamber (14) to said storing chamber (18) during an expiration cycle of said ventilator.

3. The volume ventilator of claim 2 further characterized in that said valve means actuating circuitry comprises valve enable logic apparatus (135) responsive to a receipt of binary number control signals from said calculations circuitry for supplying number control signals to said exhaust control circuitry, and said exhaust control circuitry comprises a summer circuit (146) responsive to the supplied number control signals for producing an output actual flow signal.

4. The volume ventilator of claim 3 further characterized in that said exhaust control circuitry further comprises a flow integrator (144) responsive to a receipt of an inspiration rate timing control signal from said calculations circuitry (120) for commencing an integration of said actual flow signal and a comparator (145) for comparing a calculated tidal volume signal from said calculations circuitry (120) with the integrated actual flow signal to produce a flow gate control signal as long as the calculated tidal volume signal is greater than said integrated actual flow signal and for effecting the actuation of said exhaust valve (38) during an inspiration cycle of said ventilator.

5. The volume ventilator of claim 4 further characterized in that the produced flow gate control signal enables the valve enable logic apparatus (135) to switch the binary number signals for activating a valve driver means (136) to actuate prescribed ones of the flow valve means (137–142) and thereby communicate oxygen from said source to said driving chamber (14).

6. The volume ventilator of claim 5 further comprising a nebulizer for supplying a medicinal gas flow to said driving and air/oxygen mixing means (2), and further characterized in that said control circuitry (1) further comprises nebulizer control circuitry including a nebulizer "on" signaling means (128) nebulizer flow logic (165) responsive to a receipt of an "on" signal from said signaling means (128) and a flow signal from an inspiratory flow sensor (63) in said gas flow control apparatus (3) for operating a valve driver means (136) in said valve means actuating circuitry to supply a predetermined driving gas to said nebulizer for medicinal spray mixing and entry into said driving chamber (18) during an inspiration cycle of said ventilator, and said summer circuit (146) is responsive to said nebulizer "on" signal for summing said nebulizer gas flow with said supplied number signals from said valve enable logic (135) for producing an output actual flow signal including the contribution by the nebulizer gas flow.

7. The volume ventilator of claim 5 further characterized in that said driving and air/oxygen mixing means (2) further comprises an oxygen mixing valve (45) actuatable during an inspiration cycle of said ventilator under control of said control circuitry (1) for effecting a transfer of oxygen gas from said mixing chamber (18) to said inner bellows chamber (30) in said mixing chamber (18), and said control circuitry (1) further comprises oxygen concentration control circuitry (9) responsive to said tidal volume control signal from said calculations circuitry (120) for generating a compensated tidal volume control signal and a tidal volume comparator (147) for comparing said compensated tidal volume control signal with said integrated actual flow signal from said flow integrator (144) to produce a signal for actuating said oxygen mixing valve (45) when the compensated tidal volume control signal is greater than the integrated actual flow signal and thereby effecting a transfer of oxygen gas from said mixing chamber (18) to said inner bellows chamber (30) of said bellows (20).

8. The volume ventilator of claim 7 further characterized in that said tidal volume comparator (147) interrupts the production of said oxygen mixing valve actuating signal when the compared compensated tidal volume control signal and the integrated actual flow signal are equal and thereby effects a deactuation of said oxygen mixing valve (45), and said driving and air/oxygen mixing means (2) further comprises a first check valve (54) effective subsequent to the deactuation of said mixing valve (45) for expelling oxygen gas from said mixing chamber (18) to the atmosphere.

9. The volume ventilator of claim 8 further characterized in that said spacing member (17) further comprises another bore (53) for transferring said oxygen gas from said mixing chamber (18) and said mixing valve (45) to said inner bellows chamber (30) of said mixing chamber bellows (20), and said driving and air/oxygen mixing means (2) further comprises a check valve (55) effective subsequent to the deactuation of said mixing valve (45) for drawing air into said inner bellows chamber (30) of said mixing chamber bellows (20) to mix with the oxygen therein.

10. The volume ventilator of claim 9 further characterized in that said spacing member (17) further comprises a transfer bore (40) extending between said inner bellows chamber (30) of said mixing chamber bellows (20) and said inner bellows chamber (29) of said driving chamber bellows (19), and said driving and air/oxygen mixing means (2) further comprises a check valve (39) effective for transferring an oxygen air mixture from said inner bellows chamber (30) of said mixing chamber bellows (20) to said inner bellows chamber (29) of said driving chamber bellows (19) during an expiratory cycle of said ventilator, said check valve (39) being responsive to a compression of said driving chamber bellows (19) under control of pressure on said plate member (27) in said driving chamber (14) by oxygen gas flow in said driving chamber (14) during an inspiration cycle for closing said transfer bore (40) and delivering said oxygen air mixture from said inner bellows chamber (29) of said driving chamber bellows (19) through a bore conduit (41) in said spacing member (17) to said gas flow control apparatus (3).

11. A volume ventilator for artificial ventilation of a patient during inspiration and expiration cycles of the ventilator comprising patient breathing apparatus, gas flow control apparatus operably connected to said patient breathing apparatus for supplying a delivered air/oxygen gas mixture to said breathing apparatus, a driving and air/oxygen mixing means operably connected to said flow control apparatus and controllable for delivering a prescribed mixture of air/oxygen gas to said flow control apparatus, control means operably connected to said flow control apparatus and said driving and air/oxygen mixing means including adjustment means cooperating with said flow control apparatus and said driving and air/oxygen mixing means for setting a prescribed minute volume, respiratory rate and inspiration-to-expiration ratio, said control means comprising control circuitry activated by settings of said adjustment means for controlling the driving and air/oxygen mixing means to mix and deliver said air/oxygen gas mixture to said gas flow control apparatus and for controlling the operation of said gas flow control apparatus for supplying to said patient breathing apparatus said air/oxygen gas mixture at said prescribed minute volume, respiratory rate and inspiration-to-expiration, and facilities for supplying said air/oxygen gas mixture at a continuous positive airway pressure, said facilities comprising a flexible bellows assembly having an internal storage chamber, conduit means fluidically connecting said gas flow apparatus to said internal chamber for storing therein an air/oxygen gas mixture receivable from said gas flow control apparatus during an inspiration cycle of said ventilator, means exerting a continuous positive pressure on an air/oxygen mixture stored in said internal chamber, said gas flow control apparatus comprises means for selectively coupling said air/oxygen mixture at a continuous positive airway pressure from said conduit means to said patient breathing apparatus during both inspiration and expiration cycles of said ventilator, said patient breathing apparatus comprises a device for patient breathing, an expiratory valve coupled to said device for selectively controlling the pressure against which a patient inhales and exhales, said expiratory valve comprising an inlet coupled to said device, an outlet coupled to the atmosphere and an internal chamber housing an inflatable diaphragm inflatably connected to an expiration control tube, and said gas flow control apparatus further comprises a multiport expiratory valve having a first port coupled to said expiration control tube, a second port coupled to said conduit means and a third port coupled to a patient breathing apparatus and said multiport expiratory valve being operable under control of said control circuitry during inspiration and expiration cycles of said ventilator for coupling said first port to a selectable individual one of the second and third ports for inflating said diaphragm to occlude said inlet when the pressure within the inflated diaphragm is equal to and greater than the pressure at said inlet and thereby to provide a positive pressure against which the patient inhales and exhales to the atmosphere.

12. The volume ventilator of claim 11 further characterized in that said gas flow control apparatus (3) further comprises a control valve (56) selectively actuatable under control of said control circuitry (1) for coupling said driving and air/oxygen mixing means (2) with said conduit means (79, 80) for filling said internal bellows chamber (81) during an inhalation cycle of said ventilator for maintaining said continuous positive airway pressure during inhalation and exhalation.

13. The volume ventilator of claim 12 further characterized in that said control circuitry (1) comprises a circuit arrangement (120, 135, 136, 144, 145, 146) for controlling the supply of said oxygen mixture to said patient breathing apparatus (5) and being operable for controlling the supply of a prescribed larger volume of the oxygen mixture to said driving and air/oxygen mixing means (2) for delivery to said gas flow control apparatus (3), a sensor (86) cooperating with said bellows assembly (76) for sensing a low fill of oxygen mixture in said internal chamber (81), a fill monitor circuit (134) activated by said sensor (86) in response to a sensing of the low fill in said internal chamber (81) for operating said circuit arrangement (120, 135, 136, 144–146) to effect the supply of said prescribed larger volume of oxygen mixture to said gas flow control means (3), and means (150, 151) controlled by the activation of said fill monitor circuit for actuating said control valve (56) for coupling said prescribed larger volume of oxygen from said driving and oxygen mixing means (2) to said coupling means (79, 80) for filling said internal chamber (81) of said bellows assembly (76).

14. The volume ventilator of claim 13 further characterized in that said control circuitry (1) further comprises means (151, 156) for actuating said control valve (56) and said expiratory valve (57) in an automatic mode of the ventilator operation, said control valve actuation being effective for communicating the prescribed minute volume of said oxygen mixture from said driving and oxygen mixing means (2) to said conduit means (79, 80) for storage in said internal bellows chamber (81), and said expiratory valve (57) actuation being effective to couple said internal chamber (81) to said inflatable diaphragm (75) and inflating diaphragm (75) for occulating said inlet (73) of said expiratory valve (57) and air/thereby providing a continuous positive airway pressure against which the patient inhales and exhales.

15. The volume ventilator of claim 14 further characterized in that said control circuitry (1) comprises a circuit arrangement (120, 135, 136, 144, 145, 146) for controlling the supply of said oxygen mixture to said patient breathing apparatus (5) and being operable for controlling the supply of a preprogrammed larger volume of the oxygen mixture to said driving and oxygen mixing means (2) for delivery to said gas flow control apparatus (3) when the patient inhales more than a predetermined amount of the oxygen mixture in said internal chamber (81) during the automatic mode of the ventilator operation, a sensor (86) cooperating with said bellows assembly (76) for sensing a low fill of oxygen mixture in said internal chamber (81) when a patient breathes more than the prescribed minute volume prescribed by the setting of said adjustment means, a fill monitor circuit (134) activated by said sensor (86) in response to a sensing of the low fill in said internal chamber (81) for operating said circuit arrangement (120, 135, 136, 144–146) to effect a supply of said preprogrammed larger volume of oxygen mixture to said gas flow control means (3) for communication through said control valve (56) and conduit means (79, 80) to said internal chamber (81).

16. The volume ventilator of claim 5 further characterized in that said control circuitry (1) further comprises a breathing assist sensor (88) cooperating with said bellows assembly (76) for sensing an excess fill of oxygen in said internal chamber (81) when a patient breathes less than a prescribed minute volume, and logic means activated by said assist sensor (88) sensing an excess fill of oxygen in said internal chamber (81) for deactuating said control valve (56) and switching said expiratory valve (58) for connecting said diaphragm (75) to said patient breathing passageway (92) and whereby the remaining portion of the volume of oxygen mixture from said driving and air/oxygen mixing means (2) is delivered directly to the patient through said patient breathing passageway (92) and apparatus (5) for assisted breathing.

17. The volume ventilator of claim 16 further characterized in that said logic means comprises a gating arrangement (152, 156, 151) operable for controlling said deactuation of said control valve (56) and said switching of said expiratory valve (58), a sensor (63) and inspiratory logic and comparator (154) responsive to a patient inspiratory flow in said patient breathing passageway (92) for operating said gating arrangement.

18. The volume ventilator of claim 17 further characterized in that said control circuitry (1) further comprises a control level sensor (89) cooperating with said bellows assembly (76) for sensing an excessively large fill of oxygen in said internal chamber (81) when a patient is breathing very little or not at all, and said gating arrangement (151, 156) is operated by said control level sensor (89) sensing said excessively large fill for automatically switching said ventilator from an automatic breathing mode to a control mode of operation by effecting the deactuation and closure of control valve (56) and the switching of said expiratory valve (58) for delivering the oxygen mixture from said driving and air/oxygen mixing means (2) directly to the patient through said breathing passageway (92) and apparatus (5) at the prescribed minute volume, respiratory rate and inspiration-to-expiration ratio set by said adjustment means (6, 7, 8).

19. The volume ventilator of claim 12 further characterized in that said gas flow control apparatus (3) comprises means for enabling the patient naturally to inhale the oxygen mixture in said internal chamber (81), said enabling means comprising a check valve (167) connected in parallel to and bypassing said control valve (56), and another check valve (93) serially connected with said parallel arrangement of said check valve (167) and said control valve (56) for coupling the oxygen mixture from said internal chamber (81) and said conduit means (79, 80) to said patient breathing apparatus (5).

20. A volume ventilator for artificial ventilation of a patient during inspiration and expiration cycles of the ventilator comprising patient breathing apparatus, gas flow control apparatus operably connected to said patient breathing apparatus for supplying a delivered oxygen gas mixture to said breathing apparatus, a driving and air/oxygen mixing means operably connected to said flow control apparatus and controllable for delivering a prescribed mixture of air/oxygen gas to said flow control apparatus, and control means operably connected to said flow control apparatus and said driving and air/oxygen mixing means including adjustment means cooperating with said flow control apparatus and said driving and air/oxygen mixing means for setting a prescribed minute volume, respiratory rate and inspiration-to-expiration ratio, said control means comprising control circuitry activated by settings of said adjustment means for controlling the driving and air/oxygen mixing means by controlling the flow of air and oxygen through said driving and air/oxygen mixing mixing means during an inhalation cycle of said ventilator to simultaneously receive and store a predetermined volume of oxygen gas, mix a previously stored predetermined volume of oxygen with air to provide a predetermined tidal volume of air/oxygen mixture, store said predetermined tidal volume of air/oxygen mixture, and deliver a previously stored tidal volume of air/oxygen to said gas flow control apparatus, and a continuous positive airway pressure means operably connected with said control circuitry, said gas flow control apparatus and said patient breathing apparatus for storing an oxygen gas mixture received from said gas flow control apparatus and for exerting a continuous positive pressure thereon and for subjecting said stored air/oxygen gas mixture under continuous positive pressure to said patient breathing apparatus during both inhalation and exhalation cycle of the ventilator against which a patient breathes during inhalation and exhalation.

21. The volume ventilator of claim 20 further characterized in that said control circuitry (1) includes means (88, 89, 90, 151, 156) for selectively operating said ventilator in an automatic mode in which a patient breathes spontaneously from the oxygen gas mixture stored by said continuous positive airway pressure means (4) and for cooperating with said gas flow control apparatus (3) and said continuous positive airway pressure means (4) for delivering a mandatory minute volume of the oxygen gas mixture from said continuous positive airway pressure means (4) and said driving and air/oxygen mixing means (2) through said gas flow control apparatus (3) to said patient breathing apparatus (5) when said patient breathes less than a predetermined volume of the oxygen gas mixture stored by said continuous positive airway pressure means (4).

22. A volume ventilator for artificial ventilation of a patient during inspiration and expiration cycles of the ventilator comprising patient breathing apparatus, gas flow control apparatus operably connected to said patient breathing apparatus for supplying a delivered oxygen gas mixture to said breathing apparatus, a driving and air/oxygen mixing means operably connected to said flow control apparatus and controllable for delivering a prescribed mixture of air/oxygen gas to said flow control apparatus, and control means operably connected to said flow control apparatus and said driving and air/oxygen mixing means including adjustment means cooperating with said flow control apparatus and said driving and air/oxygen mixing means for setting a prescribed minute volume, respiratory rate and inspiration-to-expiration ratio, said control means comprising control circuitry activated by settings of said adjustment means for controlling the driving and air/oxygen mixing means to mix and deliver said air/oxygen gas mixture to said gas flow control apparatus and for controlling the operation of said gas flow control apparatus for supplying to said patient breathing apparatus said air/oxygen gas mixture at said prescribed minute volume, respiratory rate and inspiration-to-expiration, and said driving and air/oxygen mixing means comprises chambers means for receiving and storing a predetermined volume of oxygen gas receivable from a source and for mixing said predetermined volume of oxygen with air to provide a predetermined tidal volume of air/oxygen mixture and delivering said air/oxygen mixture to said gas flow control means, and wherein said control circuitry is activated by settings of said adjustment means for controlling the driving and air/oxygen mixing means by controlling the flow of air and oxygen through said chamber means during an inhalation cycle of said ventilator to simultaneously receive and store a predetermined volume of oxygen gas, mix a previously stored predetermined volume of oxygen with air to provide a predetermined tidal volume of air/oxygen mixture, store said predetermined tidal volume of air/oxygen mixture, and deliver a previously stored tidal volume of air/oxygen mixture to said gas flow control means, said ventilator further comprising a continuous positive airway pressure assembly means operably connected with said gas flow control apparatus, said control circuitry and said patient breathing apparatus for providing a continuous positive airway pressure on said air/oxygen mixture in said gas flow control apparatus during both inspiration and expiration cycles of said ventilator against which a patient breathes during inhalation and exhalation, and the gas flow control apparatus comprises valve means controlled by said control circuitry for delivering to said patient breathing apparatus said air/oxygen mixture at said prescribed minute volume, respiratory rate, inspiration-to-expiration ratio and continuous positive pressure.

23. A volume ventilator for artificial ventilation of patient during inspiration and expiration cycles of the ventilator comprising patient breathing apparatus, gas flow control apparatus operably connected to said patient breathing apparatus for supplying a delivered oxygen gas mixture to said breathing apparatus, a driving and air/oxygen mixing means operably connected to said flow control apparatus and controllable for delivering a prescribed mixture of air/oxygen gas to said flow control apparatus, and control means operably connected to said flow control apparatus and said driving and air/oxygen mixing means including adjustment means for setting a prescribed minute volume, respiratory rate and inspiration-to-expiration ratio, characterized in that said control means comprises control circuitry activated by settings of said adjustment means for controlling the driving and oxygen mixing means to mix and deliver said air/oxygen gas mixture to said gas flow control apparatus and for controlling the operation of said gas flow control apparatus for supplying to said patient breathing apparatus said air/oxygen gas mixture at said prescribed minute volume, respiratory rate and inspiration-to-expiration, and said driving and air/oxygen mixing means comprise a first chamber for receiving a prescribed volume of oxygen from a source of oxygen during an inspiration cycle of the ventilator, a second chamber for storing the volume of oxygen transferrable from said first chamber during a subsequent expiration cycle of said ventilator, exhaust valve means actuatable by said control circuitry during said expiration cycle for communicating said oxygen from said first chamber to said second chamber, a third chamber for storing an oxygen mixture in response to oxygen transferrable thereto from said second chamber, transfer valve means actuatable by said control circuitry during a succeeding inspiration cycle of said ventilator for communicating oxygen from said second chamber to said third chamber, a fourth chamber for storing the oxygen mixture transferrable from said third chamber during a subsequent expiration cycle of said ventilator, and means responsive during a subsequent inspiration cycle of said ventilator for expelling said oxygen mixture from said fourth chamber to said gas flow control apparatus.

24. A volume ventilator for artificial ventilation of a patient during inspiration and expiration cycles of the ventilator comprising patient breathing apparatus, gas flow control apparatus operably connected to said patient breathing apparatus for supplying a delivered oxygen gas mixture to said breathing apparatus, a driving and air/oxygen mixing means operably connected to said flow control apparatus and controllable for delivering a prescribed mixture of air/oxygen gas to said flow control apparatus, means for supplying a source of oxygen under pressure to said driving and air/oxygen mixing means, and control means operably connected to said flow control apparatus and said driving and air/oxygen mixing means including adjustment means cooperating with said flow control apparatus and said driving and air/oxygen mixing means for setting a prescribed minute volume, respiratory rate and inspiration-to-expiration ratio, said control means comprising control circuitry activated by settings of said adjustment means for controlling the driving and air/oxygen mixing means to mix and deliver said air/oxygen gas mixture to said gas flow control apparatus and for controlling the operation of said gas flow control apparatus for supplying to said patient breathing apparatus said air/oxygen mixture at said prescribed minute volume, respiratory rate and inspiration-to-expiration, and said driving and air/oxygen mixing means comprises a driving chamber for receiving said oxygen under pressure during an inspiration cycle of the ventilator from said supplying means, a storing chamber for storing the oxygen receivable from said driving chamber, valve means controlled by said control circuitry during an expiration cycle of said ventilator for communicating the oxygen from said driving chamber to said storing chamber, a mixing bellows mounted within said storing chamber and having an interior bellows mixing chamber for storing an air/oxygen mixture, valve means controlled by said control circuitry during an inspiration cycle of said ventilator for communicating some or all of the oxygen from said storing chamber to said bellows mixing chamber, valve means actuatable during an inspiration cycle of said ventilator in response to differential pressures for exhausting oxygen in said storing chamber to the atmosphere and for mixingly admitting air into said bellows mixing chamber, a drive bellows mounted within said driving chamber and having an interior drive bellows chamber for storing an air/oxygen mixture, means operable during an expiration cycle of said ventilator for communicating the air/oxygen mixture from said bellows mixing chamber to said drive bellows chamber, means communicating the air/oxygen mixture in said drive bellows chamber to said gas flow control apparatus.

25. The volume ventilator of claim 24 further characterized in that
said driving and air/oxygen mixing means (2) further comprises
an assembly (27, 28, 31) secured to said bellows (19, 20) and being movable in a first direction during an inspiration cycle of said ventilator to compress said drive bellows (19) and expand said mixing bellows (20) in response to the receipt of said gas mixture communicated thereto by means (11, 12, 13) and a communication of said gas mixture from said mixing chamber (18) to said mixing bellows chamber (30) and
being further movable in a second direction during an expiration cycle of said ventilator to compress said mixing bellows (20) and expand said drive bellows (19) in response to a communication of said gas mixture from said driving chamber (14) to said mixing chamber (18) and a communication of said gas mixture from said mixing bellows chamber (30) to said drive bellows chamber (29).

26. The volume ventilator of claim 25 further characterized in that
said driving and air/oxygen mixing means (2) further comprises
a spacing member (17) separating said driving chamber (14) from said mixing chamber (18) and spaced between said drive bellows chamber (29) and said mixing bellows chamber (30),
said spacing member (17) comprising
a first bore (53) coupled to said valve apparatus (45) for communicating said gas mixture from said mixing chamber (18) to said bellows mixing chamber (30),
a second bore (40) coupled to said communicating means (39, 40) for communicating the oxygen gas mixture from said bellows mixing chamber (30) to said drive bellows chamber (29), and
a third bore (41) for communicating said oxygen gas mixture from said drive bellows chamber (29) to said gas flow control apparatus (3).

27. The volume ventilator of claim 26 further characterized in that
said assembly comprises
plate members (27, 28) each of which is secured to a respective individual movable end (25, 26) of an individual one of said bellows (19, 20) for providing said respective drive bellows chamber (29) and mixing bellows chamber (30) and
a rigid rod (31) movably extending through a fourth bore (32) of said spacing member (17) and secured at ends (33, 34) of said rod (31) to facing surfaces (35, 36) of said plate members (27, 28) for the compression and expansion of said drive bellows (19) and said mixing bellows (20).

28. A volume ventilator for artificial ventilation of a patient during inspiration and expiration cycles of the ventilator comprising
patient breathing apparatus,
gas flow control apparatus operably connected to said patient breathing apparatus for supplying a delivered air/oxygen gas mixture to said breathing apparatus,
a driving and air/oxygen mixing means operably connected to said flow control apparatus and controllable for delivering a prescribed mixture of air/oxygen gas to said flow control apparatus,
said driving and air/oxygen mixing means comprises
chamber means for receiving and storing a predetermined volume of oxygen gas receivable from a source and for mixing said predetermined volume of oxygen with air to provide a predetermined tidal volume of air/oxygen mixture and delivering said air/oxygen mixture to said gas flow control apparatus, and
control means operably connected to said flow control apparatus and said driving and air/oxygen mixing means including
adjustment means cooperating with said flow control apparatus and said driving and air/oxygen mixing means for setting a prescribed minute volume, respiratory rate and inspiration-to-expiration ratio,
said control means further comprising control circuitry activated by settings of said adjustment means for controlling the driving and air/oxygen mixing means by controlling the flow of air and oxygen through said chamber means during an inhalation cycle of said ventilator to simultaneously receive and store a predetermined volume of oxygen gas, mix a previously stored predetermined volume of oxygen with air to provide a predetermined volume of air/oxygen mixture, store said predetermined volume of air/oxygen mixture, and deliver a previously stored tidal volume of air/oxygen mixture to said gas flow control apparatus,
said control circuitry comprises
calculations circuitry responsive to settings of said adjustment means for furnishing control signals for determining prescribed minute volume, respiratory rate and inspiration-to-expiration and the air/oxygen concentration of said predetermined volume of air/oxygen gas mixture, and
said driving and air/oxygen mixing means comprises a delivery chamber fluidically connected to said gas flow control apparatus and a driving chamber operably connected to said delivery chamber for forcing air/oxygen mixture from said delivery chamber,
further comprising
a plurality of flow valve means actuable for delivering oxygen gas from a source to said driving chamber, and
said control circuitry further comprises circuitry responsive to furnished ones of said control signals for actuating predetermined ones of said valve means for delivering said oxygen gas to said driving chamber during an inspiration cycle of said ventilator.

29. A volume ventilator for artificial ventilation of a patient during inspiration and expiration cycles of the ventilator comprising
patient breathing apparatus,
gas flow control apparatus operably connected to said patient breathing apparatus for supplying a delivered oxygen gas mixture to said breathing apparatus,
a driving and air/oxygen mixing means operably connected to said flow control apparatus and controllable for delivering a prescribed mixture of air/oxygen gas to said flow control apparatus, and
said driving and air/oxygen mixing means comprises
chamber means for receiving and storing a predetermined volume of oxygen gas receivable from a source and for mixing said predetermined volume of oxygen with air to provide a predetermined tidal volume of air/oxygen mixture and delivering said air/oxygen mixture to said gas flow control apparatus, and control means operably connected to said flow control apparatus and said driving and air/oxygen mixing means including adjustment means cooperating with said flow control apparatus and said driving and air/oxygen mixing means for setting a prescribed minute volume, respiratory rate and inspiration-to-expiration ratio, characterized in that said control means comprising control circuitry activated by settings of said adjustment means for controlling the driving and air/oxygen mixing means by controlling the flow of air and oxygen through said chamber means during an inhalation cycle of said ventilator to simultaneously receive and store a predetermined volume of oxygen gas, mix a previously stored predetermined volume of oxygen with air to provide a predetermined tidal volume of air/oxygen mixture, store said predetermined tidal volume of air/oxygen mixture, and deliver a previously stored tidal volume of air/oxygen mixture to said gas flow control apparatus, facilities for supplying said air/oxygen gas mixture at a continuous positive airway pressure, and said control circuitry selectively operates said driving and air/oxygen mixing means, gas flow control apparatus, facilities and the patient breathing apparatus in an automatic mode for delivering a mandatory volume of said air/oxygen gas mixture at said continuous positive airway pressure to said patient breathing apparatus for patient ventilation even if the patient respiratory drive ceases completely.

30. A volume ventilator for artificial ventilation of a patient during inspiration and expiration cycles of the ventilator comprising patient breathing apparatus, gas flow control apparatus operably connected to said patient breathing apparatus for supplying a delivered air/oxygen gas mixture to said breathing apparatus, a driving and air/oxygen mixing means operably connected to said flow control apparatus and controllable for delivering a prescribed mixture of air/oxygen gas to said flow control apparatus, said driving and air/oxygen mixing means comprises chamber means for receiving and storing a predetermined volume of oxygen gas receivable from a source and for mixing said predetermined volume of oxygen with air to provide a predetermined tidal volume of air/oxygen mixture and delivering said air/oxygen mixture to said gas flow control apparatus, and control means operably connected to said flow control apparatus and said driving and air/oxygen mixing means including adjustment means cooperating with said flow control apparatus and said driving and air/oxygen mixing means for setting a prescribed minute volume, respiratory rate and inspiration-to-expiration ratio, said control means comprising control circuitry activated by settings of said adjustment means for controlling the driving and air/oxygen mixing means by controlling the flow of air and oxygen through said chamber means during an inhalation cycle of said ventilator to simultaneously receive and store a predetermined volume of oxygen gas, mix a previously stored predetermined volume of oxygen with air to provide a predetermined tidal volume of air/oxygen mixture, stored said predetermined tidal volume of air/oxygen mixture and deliver a previously stored tidal volume of air/oxygen mixture to said gas flow control apparatus, and said ventilator is equipped with facilities for supplying said air/oxygen mixture at a continuous positive airway pressure, said facilities comprising a flexible bellows assembly having an internal storage chamber, conduit means fluidically connecting said gas flow apparatus to said internal chamber for storing therein an air/oxygen gas mixture receivable from said gas flow control apparatus during an inspiration cycle of said ventilator and means exerting a continuous positive pressure on an air/oxygen mixture stored in said internal chamber, and said gas flow control apparatus comprises means for selectively coupling said air/oxygen mixture at a continuous positive airway pressure from said conduit means to said patient breathing apparatus during both inspiration and expiration cycles of said ventilator.

* * * * *